United States Patent [19]

Malabarba et al.

[11] Patent Number: 4,684,644

[45] Date of Patent: Aug. 4, 1987

[54] BASIC MONOCARBOXYAMIDE DERIVATIVES OF ACTAGARDINE HAVING ANTIBIOTIC ACTIVITY AND COMPOSITIONS THEREOF

[75] Inventors: Adriano Malabarba; Bruno Cavalleri, both of Milan, Italy

[73] Assignee: Gruppo Lepetit S.p.A., Gerenzano, Italy

[21] Appl. No.: 842,523

[22] Filed: Mar. 21, 1986

[30] Foreign Application Priority Data

Mar. 22, 1985 [GB] United Kingdom ............... 8507528

[51] Int. Cl.$^4$ ............... A61K 35/74; A61K 35/00; C07D 295/14

[52] U.S. Cl. .................. 514/210; 514/222; 514/228; 514/252; 514/255; 514/316; 514/331; 514/422; 514/428; 514/542; 514/550; 514/562; 514/570; 424/117; 544/58.1; 544/58.5; 544/58.6; 544/85; 544/111; 544/121; 544/130; 544/141; 544/159; 544/357; 544/359; 544/360; 544/364; 544/372; 544/400; 546/190; 546/208; 546/233; 548/523; 548/567; 548/568; 548/950; 560/9; 560/147; 562/426; 562/556

[58] Field of Search ............ 544/58.1, 58.5, 58.6, 544/85, 111, 121, 130, 141, 159, 357, 359, 360, 364, 372, 400; 546/190, 208, 233; 548/523, 567, 568, 950; 560/9, 147; 562/426, 556; 424/117; 514/210, 222, 228, 252, 255, 316, 331, 422, 428, 542, 550, 562, 570

[56] References Cited

U.S. PATENT DOCUMENTS 4,022,884  5/1977  Parenti et al. .............. 424/117

OTHER PUBLICATIONS

Malabarba et al., Chemical Abstracts, vol. 104, (1986), No. 48401z.

Primary Examiner—Robert W. Ramsuer
Attorney, Agent, or Firm—Stephen L. Nesbitt

[57] ABSTRACT

The present invention is directed to a class of basic monocarboxyamide derivatives of actagardine. Actagardine (INN) is an antibiotic substance produced by actinoplanes strains such as *Actinoplanes Sp.* ATCC 31048 and *Actinoplanes Sp.* ATCC 31049 which are described in U.S. Pat. No. 4,022,884. Actagardine shows antimicrobial in vitro and in vivo activity against gram-positive organisms. Its complete chemical structure is not yet known but there is only information on its chemical functions and main fragments. In particular, it has been found that actagardine has two carboxylic functions and a primary amino function and can therefore be represented as follows:

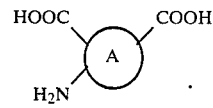

The compounds of the invention are monoamide derivatives at one of the carboxy functions of actagardine. More particularly, they are basic monoamide derivatives of actagardine which may be schematically represented by the following formula I:

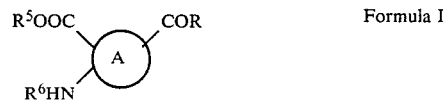

Formula I

The compound of the invention possess improved antimicrobial activity in particular against gram positive bacteria.

7 Claims, No Drawings

BASIC MONOCARBOXYAMIDE DERIVATIVES OF ACTAGARDINE HAVING ANTIBIOTIC ACTIVITY AND COMPOSITIONS THEREOF

The present invention is directed to a class of basic monocarboxyamide derivatives of actagardine. Actagardine (INN) is an antibiotic substance produced by actinoplanes strains such as *Actinoplanes Sp.* ATCC 31048 and *Actinoplanes Sp.* ATCC 31049 which are described in U.S. Pat. No. 4,022,884.

Actagardine shows antimicrobial in vitro and in vivo activity against gram-positive organisms. Its complete chemical structure is not yet known but there is only information on its chemical functions and main fragments. In particular, it has been found that actagardine has two carboxylic functions and a primary amino function and can therefore be represented as follows:

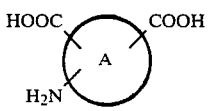

The compounds of the invention are monoamide derivatives at one of the carboxy functions of actagardine. More particularly, they are basic monoamide derivatives of actagardine which may be schematically represented by the following formula I:

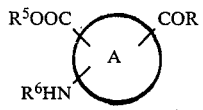

Formula I wherein

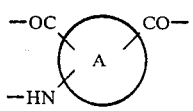

represents the actagardine nucleus, R represents the group

$R^1$ and $R^2$ independently represent hydrogen, a group of formula

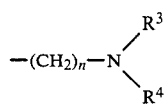

in which n represents an integer from 2 to 8 and $R^3$ and $R^4$ independently represent hydrogen or $(C_1-C_4)$ alkyl or $R^3$ and $R^4$ taken together represent a $-(CH_2)_3-$, $-(CH_2)_4-$, $(CH_2)_2-O-(CH_2)_2$, $-(CH_2)_2-S-(CH_2)_2-$ or $-(CH_2)_5-$ group, or $R^1$ and $R^2$ taken together with the adjacent nitrogen atom represent a piperazine moiety which may be substituted in position 4 with a substituent selected from $(C_1-C_4)$alkyl, $(C_5-C_7)$-cycloalkyl, pyridyl, benzyl, and substituted benzyl wherein the phenyl moiety bears 1 or 2 substituents selected from chloro, bromo, nitro, $(C_1-C_4)$alkyl and $(C_1-C_4)$alkoxy, $R^5$ represents hydrogen, $(C_1-C_4)$alkyl or $(C_1-C_4)$alkoxy $(C_2-C_4)$alkyl, $R^6$ represent hydrogen or $(C_1-C_4)$alkyl with the proviso that $R^1$ and $R^2$ can not simultaneously represent hydrogen, and the acid and base addition salts thereof.

The term "$(C_1-C_4)$alkyl" represents straight or branched alkyl chains of from 1 to 4 carbon atoms, such as: methyl, ethyl, propyl, 1-methylethyl, butyl, 1-methylpropyl or 1,1-dimethylethyl while the term "$C_2-C_4$)alkyl" represents straight or branched alkyl chains of from 2 to 4 carbon atoms such as: ethyl, propyl, 1-methylethyl, butyl, 1-methylpropyl or 1,1-dimethylethyl. The term "$(C_5-C_7)$cycloalkyl" represents a cycloalkyl group selected from cyclopentyl, cyclohexyl and cycloheptyl.

The term "$(C_1-C_4)$alkoxy" represents a straight or branched alkoxy chain of 1 to 4 carbon atoms such as methoxy, ethoxy, propoxy, 1-methylethoxy, butoxy, 1-methylpropoxy and 1,1-dimethylethoxy. The compounds of the invention possess acid and basic functions capable of forming salts. These salts can be prepared according to techniques well known in the art.

Examples of acid addition salts of the invention are: hydrohalides, such as the hydrochloride and hydrobromide, sulfate, phosphate, nitrate, acetate, citrate, aspartate, methanesulfonate and toluenesulfonate.

Examples of salts with bases include the alkali metal and alkaline earth metal salts such as the sodium, potassium, lithium, magnesium, zinc, and calcium salts. The transformation of the non-salt form of a compound of the invention in a salt thereof, by adding the selected base or acid, and the reverse i.e. the transformation of an addition salt of a compound of the invention into the non-salt form, are within ordinary technical skill and are encompassed by the present invention.

In view of the similarity of the properties of the compounds of formula I and their salts, what is said in the present application when dealing with the biological activities of the compounds of formula I applies also to their pharmaceutically acceptable salts, and vice versa.

Representative examples of the derivatives of the invention are the actagardine derivatives wherein the monoamide mojety has the formula —COR wherein R represents:

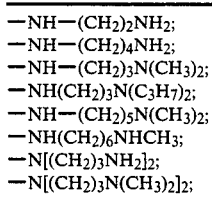 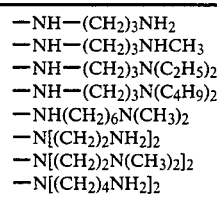

| | |
|---|---|
| —NH—(CH₂)₂NH₂; | —NH—(CH₂)₃NH₂ |
| —NH—(CH₂)₄NH₂; | —NH—(CH₂)₃NHCH₃ |
| —NH—(CH₂)₃N(CH₃)₂; | —NH—(CH₂)₃N(C₂H₅)₂ |
| —NH(CH₂)₃N(C₃H₇)₂; | —NH—(CH₂)₃N(C₄H₉)₂ |
| —NH—(CH₂)₅N(CH₃)₂; | —NH(CH₂)₆N(CH₃)₂ |
| —NH(CH₂)₆NHCH₃; | —N[(CH₂)₂NH₂]₂ |
| —N[(CH₂)₃NH₂]₂; | —N[(CH₂)₂N(CH₃)₂]₂ |
| —N[(CH₂)₃N(CH₃)₂]₂; | —N[(CH₂)₄NH₂]₂ |

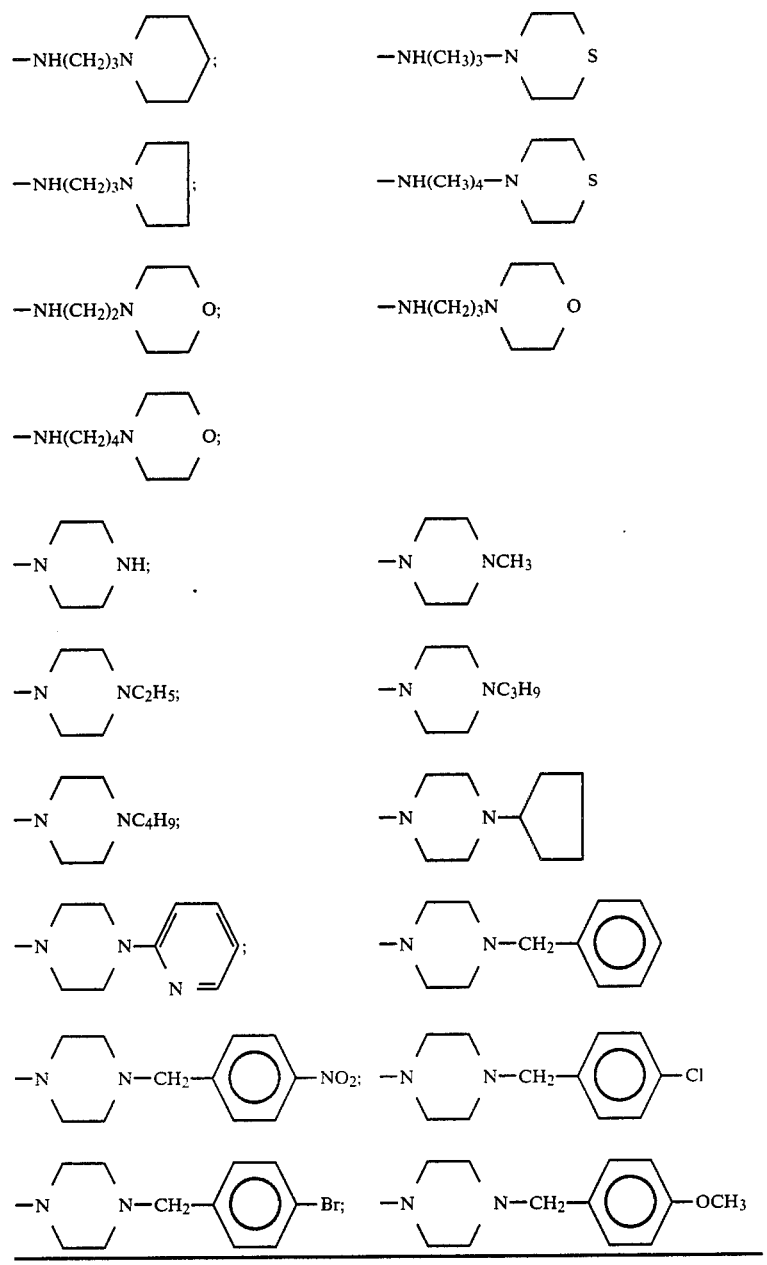

The monoamide derivatives of the invention are prepared by reacting actagardine with a 2 to 6-fold molar excess of the selected amine of formula $HNR^1R^2$, wherein $R^1$ and $R^2$ are as defined above, in a suitable inert organic solvent such as dimethylformamide (DMF) at a temperature between 0° C. and room temperature and in the presence of a suitable condensing agent.

When the amine $R^1R^2NH$ contains a further primary amino group it should be protected, as known in the art, in order to get the desired product. Obviously, a deprotection step is then necessary to obtain the desired final product.

Representative examples of condensing agents are ($C_1$–$C_4$)alkyl or phenyl phosphorazidates such as, diphenyl phosphorazidate (DPPA), diethyl phosphorazidate, di(4-nitrophenyl) phosphorazidate, dimorpholyl phosphorazidate and diphenyl phosphorochloridate. The preferred condensing agent is diphenyl phosphorazidate (DPPA).

A preferred molar excess of the selected amine over actagardine is from 3 to 5 mole of amine per mole of actagardine, while the preferred molar excess is a 4-fold molar excess.

The condensing agent is generally present in a slight molar excess, preferably from 1.1 to 3 mole per mole of actagardine.

The reaction temperature is preferably from 0° C. to 25°–30° C. The preferred temperature range is from 0° C. to 5° C.

The reaction can be monitored by TLC or HPLC. A preferred TLC technique includes the use of silica gel plates (such as Silica-gel $F_{254}$ plates, Merck) with a mixture $CH_3CN:0.1M$ phosphate buffer pH 7.0, at a ratio of 75 to 25 (v/v) for the piperazinyl derivatives, and at a ratio 60 to 40 (v/v) for the others as the developing mixture. The spots may be detected by both UV light at 254 nm and by charring with conc. $H_2SO_4$ at 120° C.

When the amine $R^1R^2NH$ is reacted as a corresponding salt, e.g. the hydrochloride, it is necessary to add a suitable base in at least a molar proportion to obtain the free base of the amine $R^1R^2NH$ which reacts with actagardine. In this case, an excess of the base is generally preferred. Examples of bases suitable to free the amine $R^1R^2NH$ from its salts include tertiary amine such as triethylamine or trimethylamine, picoline and the like. As already said, when the amine $R^1R^2NH$ contains a further primary amino group, it is necessary to protect it before reacting it with actagardine. The protection of the primary amino group (or groups) is made according to known per se techniques. A preferred way of protecting the primary amino function is by reaction with benzaldehyde in ethanol at room temperature to form the benzylidene derivative which is then reacted with actagardine as described above. Once the reaction is completed, the protecting group can easily be removed for example by treating with diluted hydrochloric acid at room temperature.

In so doing, a compound of formula I is obtained wherein R is as defined, and $R^5$ and $R^6$ are hydrogen atoms or the corresponding salts.

The acid-base titration of these basic monoamide derivatives show that indeed only one amidic bond is formed while the other carboxylic function of actagardine remains unreacted. This method of forming the amide derivative invention is therefore a selective method for preparing a mono-amide derivative of actagardine without forming the possible diamide derivative.

The compound of the invention wherein $R^5$ and/or $R^6$ are as defined above but different from hydrogen are prepared by reacting the corresponding compound wherein $R^5$ and/or $R^6$ are hydrogen with a suitable esterifying or alkylating agent.

Suitable esterifying agents are acidic mixture of the selected alcohol of formula $R^5OH$. The reaction is generally conducted in an excess of the alcoholic solution which acts also as the reaction solvent. The temperature is in general about room temperature but temperatures between 5° C. and 40° C. may be used. The reaction time varies depending on the other reaction parameters, but in general the reaction is completed in 4–48 h. The reaction is in any case monitored by TLC procedures which employ polar mixtures such as methanol/phosphate buffer pH 7, 7:3 (v/v) or butanol/acetic acid/water, 4:1:1 (v/v) and UV visualization at 254 nm or carbonization at 120° C. with conc. $H_2SO_4$.

The alkylation of the primary amino group of actagardine is preferably carried out by reductive alkylation using the corresponding carbonylic compound to form a Shiff base which is then reduced in the presence of a suitable reducing agent such as a borohydride derivative, e.g. sodium borohydride or potassium borohydride, to give the desired $R^6$ alkyl residue. As it is evident, the skilled man is capable of selecting the carbonylic compound which, upon reduction, will give the desired alkyl group represented by the symbol $R^6$. The formation of the Shiff base occurs preferably in a polar aprotic solvent such as a lower alcohol, e.g. methanol or ethanol. The reaction is preferably conducted at about 0° C. Also the reduction step is preferably conducted at about 0° C., while is generally preferred to increase the temperature to at least room temperature to complete the reaction.

The following tables reports the physico-chemical parameters of representative examples of the compounds of the invention.

TABLE I

| COMPOUND No. | di-amine reactant (RH) | R | R⁵ | R⁶ | Formula[1] (MW) | Analytical results[2] (calcd/found) C | H | N | S |
|---|---|---|---|---|---|---|---|---|---|
| I | $NH_2CH_2CH_2NH_2$ | $NHCH_2CH_2NH_2$ | H | H | $C_{89}H_{148}N_{22}O_{24}S_4$ (2038) | 52.45 / 51.25 | 7.32 / 7.09 | 15.12 / 15.36 | 6.29 / 5.98 |
| II | $NH_2(CH_2)_4NH_2$ | $NH-(CH_2)_4NH_2$ [3] | H | H | $C_{91}H_{152}N_{22}O_{24}S_4$ (2066) | 52.90 / 51.96 | 7.41 / 7.07 | 14.91 / 15.57 | 6.21 / 5.90 |
| IIIa | $NH_2(CH_2)_3N(CH_3)_2$ | $NHCH_2CH_2CH_2N(CH_3)_2$ | H | H | $C_{92}H_{156}N_{22}O_{24}S_4$ (2083) | 53.06 / 52.83 | 7.55 / 7.56 | 14.80 / 14.73 | 6.16 / 6.04 |
| IIIb | $NH_2(CH_2)_3N(CH_3)_2$ | $NHCH_2CH_2CH_2N(CH_3)_2 \cdot HCl$ [4] | H | H | $C_{92}H_{157}ClN_{22}O_{24}S_4$ (2119) | 52.14 / 52.20 | 7.47 / 7.49 | 14.54 / 14.61 | 6.05 / 5.91 |
| IV | $HN[CH_2CH_2N=CH\text{-}Ph]_2$ | $N(CH_2CH_2NH_2)_2$ | H | H | $C_{91}H_{152}N_{23}O_3O_{24}S_4$ (2080) | 52.53 / 50.07 | 7.36 / 7.00 | 16.48 / 15.73 | 6.16 / 6.57 |
| V | $HN[CH_2CH_2N(CH_3)_2]_2$ | $N(CH_2CH_2N(CH_3)_2)_2$ | H | H | $C_{95}H_{161}N_{23}O_{24}S_4$ (2137) | 53.38 / 52.84 | 7.59 / 7.25 | 15.07 / 15.21 | 6.00 / 6.38 |
| VI | piperazine (N—H) | piperazinyl (N—H) | H | H | $C_{91}H_{150}N_{22}O_{24}S_4$ (2064) | 52.95 / 52.58 | 7.32 / 7.14 | 14.93 / 15.46 | 6.21 / 6.73 |
| VII | N-methylpiperazine | N-methylpiperazinyl | H | H | $C_{92}H_{152}N_{22}O_{24}S_4$ (2079) | 53.15 / 53.13 | 7.36 / 7.15 | 14.82 / 15.53 | 6.17 / 6.43 |
| VIII | N-cyclopentylpiperazine | N-cyclopentylpiperazinyl | H | H | $C_{96}H_{158}N_{22}O_{24}S_4$ (2132) | 54.08 / 53.66 | 7.47 / 7.27 | 14.45 / 15.00 | 6.02 / 6.61 |
| IX | N-benzylpiperazine | N-benzylpiperazinyl | H | H | $C_{98}H_{156}N_{22}O_{24}S_4$ (2154) | 54.64 / 55.19 | 7.30 / 7.19 | 14.30 / 14.68 | 5.95 / 6.23 |
| ACTAGARDINE | | | H | H | $C_{87}H_{142}N_{20}O_{25}S_4$ (1996) | — / 52.03 | — / 7.14 | — / 14.32 | — / 6.40 |
| X | $NHCH_2CH_2NH_2$ | | $CH_2CH_2OCH_3$ | H | $C_{92}H_{154}N_{22}O_{25}S_4$* (2096) | | | | |

TABLE I-continued

| COMPOUND No. | di-amine reactant (RH) | R | R⁵ | R⁶ | Formula⁽¹⁾ (MW) | Analytical results⁽²⁾ (calcd/found) C H N S |
|---|---|---|---|---|---|---|
| XI | | NHCH₂CH₂N(CH₃)₂ | CH₃ | H | C₉₃H₁₅₈N₂₂O₂₄S₄* (2097) | |
| XII | | NHCH₂CH₂N(CH₃)₂ | C₂H₅ | H | C₉₄H₁₆₀N₂₂O₂₄S₄* (2111) | |
| XIII | | NHCH₂CH₂N(CH₃)₂ | H | C₂H₅ | C₉₄H₁₆₀N₂₂O₂₄S₄ (MW 2111) | |
| XIV | | N⟨piperazinyl⟩N—CH₃ | CH₃ | H | C₉₃H₁₅₄N₂₂O₂₄S₄* (2093) | |
| XV | | N⟨piperazinyl⟩N—CH₃ | C₂H₅ | H | C₉₄H₁₅₆N₂₂O₂₄S₄* (2107) | |
| XVI | | N⟨piperidinyl⟩N | CH₃ | H | C₉₇H₁₆₀N₂₂O₂₄S₄* (2146) | |
| XVII | | N⟨piperidinyl⟩N | C₂H₅ | H | C₉₈H₁₆₂N₂₂O₂₄S₄* (2160) | |

Notes to TABLE I:
*Elemental analysis confirms the assigned formula.
⁽¹⁾The theoretical formulas of the derivatives were calculated assuming the formula C₈₇H₁₄₂N₂₀O₂₅S₄ for actagardine. The compounds melted with decomposition over a range of temperatures from 200° to 300° C.
⁽²⁾Analyses were carried out on the products dried at 150° under nitrogen atmosphere. The purity of the derivatives (expressed as percentages of the areas of the chromatographic peaks) was determined by HPLC in reverse phase partition with a Waters chromatograph equipped with pump mod. M45, Rheodyne valve mod. 7125 (20 μl loop), UV detector mod. 440 at 254 nm (1.10⁻² UA) connected to data system SP 4000 (Spectra Physics). The column (25 cm × 4.6 mm i.d.), prepacked with Lichrosorb RP-8 10 μm, was used at room temperature with 0.1 M phosphate buffer pH 7.5/CH₃CN 60:40 (v/v) as the mobile phase and with a flow rate of 1 ml/min. Purity of the compounds according to this method was almost always higher than 94%. In particular, the purity of derivative IIIb resulted 97%. The inorganic residue found (after heating at 900° C.) in oxygen atmosphere was always less than 0.5%.
⁽³⁾Purity (HPLC) ~ 90%.
⁽⁴⁾Cl %: calculated 1.67, found 1.58

TABLE II

| Compound No. | Solubility[1] in water (mg/ml) pH 7.3 | Solubility[1] in water (mg/ml) pH 4.0 | Acid-base Titration[2] E W HTBA | Acid-base Titration[2] E W HClO$_4$ | pk$_2$[4] (MCS/H$_2$O) | Partition Coeff.[3] (log P) CH$_3$(CH$_2$)$_7$OH/H$_2$O H$_2$O[5] | Partition Coeff.[3] (log P) CH$_3$(CH$_2$)$_7$OH/H$_2$O pH 3[6] |
|---|---|---|---|---|---|---|---|
| I | 20 | 80 | 2400 | 1154 | 9.7 | −0.174 | −0.973 |
| II | 30 | 100 | n.d. | 1058 | 9.8 | −0.468 | −0.922 |
| IIIa | 200 | 600 | n.d. | 1142 | 9.2 | −0.790 | −1.644 |
| IIIb | 200 | 600 | 1082 | 2119(7) | 9.2 | n.d. | −1.644 |
| IV | n.d. | 100 | n.d. | 750 | n.d. | −0.680 | −1.353 |
| V | n.d. | 200 | n.d. | 814 | n.d. | −0.066 | n.d. |
| VI | <10 | 60 | 2289 | 1098 | 8.4 | −0.133 | −0.733 |
| VII | <10 | 45 | 2084 | 1036 | 7.5 | 0.214 | −0.955 |
| VIII | <10 | 20 | 2160 | 1038 | 7.5 | 1.084 | −0.562 |
| IX | <10 | 20 | 2037 | 905 | 7.2 | n.d. | −0.145 |
| ACTAGARDINE | 70 | <10 | 985 | 1950 | — | (−0.545)[8] | 0.357 |

| Compound No. | Acid-base Titration E W HTBA | Acid-base Titration E W HClO$_4$ | 0.1 N NaOH | 0.1 N HCl |
|---|---|---|---|---|
| X | (no titrable functions) | 1068 (2 basic functions) | — | — |
| XI | " | 1161 (2 basic functions) | — | — |
| XII | " | 1198 (2 basic functions) | — | — |
| XIII | 2074 | 1039 (2 basic functions) | 2091 | 1052 |
| XIV | (no titrable functions) | 1065 (2 basic functions) | — | — |
| XV | " | 1084 (2 basic functions) | — | — |
| XVI | " | 1107 (2 basic functions) | — | — |
| XVII | " | 1099 (2 basic functions) | — | — |

Notes to Table II:
[1] Approximate values.
[2] Acid-base titrations were carried out in both aqueous [methylcellosolve (MCS): water 4:1 (v/v)] and non-aqueous [pyridine or acetic acid] solvents. The pK$_{MCS}$ values (pK$_2$) of the additional basic functions were determined in MCS:H$_2$O 4:1 (v/v) solution by titration of the compounds with 0.01 N Na OH. The presence of the free amino group of actagardine (pK$_{MCS}$ 6.3) in the derivatives, except compound XIII, was confirmed by titration with 0.01 N HCl. Compound XIII did not show this pKa value but a pKa value between 8.9 and 9.4. The equivalent weights (E W) were obtained by titration with either hydroxytetrabutylamine (HTBA) in pyridine or perchloric acid (HClO$_4$) in acetic acid.
[3] Partition coefficients (log P) were determined between n-octanol and water. The concentration of the compounds in each phase was determined spectrophotometrically (UV).
[4] All compounds possess also the ionizable basic function of actagardine (pK$_{MCS}$ 6.3) unmodified. Titration in MCS:H$_2$O 4:1 (v/v) with 0.01 N HCl.
[5] Distilled water.
[6] 0.1 M acetate buffer pH 3.0.
[7] Values determined in MCS:H$_2$O 4:1 (v/v) by titration with either 0.1 N NaOH or 0.1 N HCl.
[8] Actagardine (acid form) is not soluble in water. The value given is log P between n-octanol and 0.1 M phosphate buffer pH 7.3.
n.d. = not determined.
MCS = methylcellosolve;

TABLE III

Spectral data

| Compound No. | IR (ν,cm$^{-1}$)[1] νN—H | amide I | amide II | amide III | γC—N (aromatic) | νC—N (piperazine) | νC—S | UV[2] λmax.nm (E$^{1\%}_{1\,cm}$) |
|---|---|---|---|---|---|---|---|---|
| I | 3280 | 1650 | 1525 | 1240 | — | — | 740 | 280 (21.00) |
| II | 3280 | 1650 | 1525 | 1240 | — | — | 740 | 280 (19.11) |
| III (a,b) | 3280 | 1650 | 1515 | 1235 | — | — | 735 | a.282 (26.50) b.279 (22.36) |
| IV | 3290 | 1655 | 1525 | 1240 | — | — | 740 | 279 (25.67) |
| V | 3290 | 1650 | 1525 | 1240 | — | — | 740 | 279 (25.04) |
| VI | 3300 | 1655 | 1530 | 1240 | — | 1030 | 740 | 280 (22.12) |
| VII | 3300 | 1655 | 1525 | 1235 | — | 1030,1000 | 740 | 280 (24.08) |
| VIII | 3300 | 1650 | 1530 | 1245 | — | 1030 | 740 | 280 (22.00) |
| IX | 3300 | 1655 | 1520 | 1235 | 700 | 1030,1000 | 740 | 278 (23.14) |
| Actagardine | 3300,3060 | 1660 | 1525 | 1235 | — | — | 740 | 278 (26.00) |

| Compound No. | (ν, cm$^{-1}$)[1] νN—H | amide I | amide II | amide III | νCO (ester) | γC—H (arom.) | νC—N (piperazine) | νC—S |
|---|---|---|---|---|---|---|---|---|
| X | 3280 | 1650 | 1525 | 1240 | 1730 | — | — | 740 |
| XI | 3280 | 1650 | 1515 | 1235 | 1730 | — | — | 735 |
| XII | 3280 | 1650 | 1515 | 1235 | 1730 | — | — | 735 |
| XIV | 3300 | 1655 | 1525 | 1235 | 1730 | — | 1030,1000 | 740 |
| XV | 3300 | 1655 | 1525 | 1235 | — | — | 1030,1000 | 740 |
| XVI | 3300 | 1650 | 1530 | 1245 | 1730 | — | 1030 | 740 |
| XVII | 3300 | 1650 | 1530 | 1245 | 1730 | — | 1030 | 740 |

Notes to Table III:
[1] IR spectra were recorded with a Perkin-Elmer mod. 580 spectrophotometer in nujol mull.
[2] UV spectra were recorded with a Perkin-Elmer mod. 320 UV-VIS spectrophotometer in methanol solution.

The compounds of the invention show antibacterial activity in vitro and in vivo. They are most active against S. mitis, S. salivarius, and S. pyogenes, including clinical isolates of these strains. They have, in general, ameliorated activity compared to actagardine.

Minimal inhibitory concentration (MIC) are determined by the twofold serial dilution method in Brain heart infusion broth (Difco); it is supplemented with 2% bovine serum when streptococci are tested. The inoculum size is about $10^3$ colony units per ml (CFU/ml). The MIC is defined as the lowest concentration which prevents visible growth after overnight incubation at 37° C. The influence of serum is determined on S. aureus Tour by adding 30% bovine serum to the medium. Inoculum size ($\sim 10^6$ CFU/ml) and 30% bovine serum did not influence the antibacterial activity at a great extent; the MIC found in the presence of serum were generally lower than those without it. The antimicrobial activities of the compounds of the invention in comparison with reference compound (actagardine) are reported in the following Table IV:

| Compound No. | Infecting Strain | | $ED_{50}$ (mg/Kg) |
|---|---|---|---|
| I | S. pyogenes | C 203 | 0.14 |
| II | S. pyogenes | C 203 | 0.19 |
| III (b) | S. pyogenes | C 203 | 0.47 |
|  | S. pneumoniae | UC41 | 3.5 |
| IV | S. pyogenes | C 203 | 0.62 |
| V | S. pyogenes | C 203 | 0.29 |
| VI | S. pyogenes | C 203 | 0.25 |
| VII | S. pyogenes | C 203 | 0.24 |
| VIII | S. pyogenes | C 203 | 0.22 |
| IX | S. pyogenes | C 203 | 0.2 |
| XIII | S. pyogenes | C 203 | 0.23 |
| ACTAGARDINE | S. pyogenes | C 203 | 0.81 |

The antibacterial activity of compound III (a and b) was compared with that of actagardine against growing

TABLE IV

In vitro Anitbacterial Activity (MIC, µg/ml)

| MICROORGANISM | | I | II | III(a,b) | IV | V | VI | VII | VIII | IX | acta-gardine |
|---|---|---|---|---|---|---|---|---|---|---|---|
| S. aureus TOUR | $10^{3(1)}$ | 6.2 | 6.2 | 12.5 | 50 | 50 | 25 | 12.5 | 25 | 6.2 | 25 |
|  | $10^{6(1)}$ | 25 | 25 | 25 | 50 | 50 | 50 | 25 | 50 | 12.5 | 50 |
|  | + serum$^{(2)}$ | 3.1 | 3.1 | 6.2 | 12.5 | 12.5 | 25 | 12.5 | 12.5 | 6.2 | 25 |
| S. pyogenes | C 203 | 0.2 | 0.2 | 0.4 | 0.8 | 0.8 | 0.4 | 0.8 | 0.4 | 0.8 | 1.6 |
| S. pneumoniae | UC 41 | 12.5 | 12.5 | 6.2 | 12.5 | 25 | 6.2 | 6.2 | 6.2 | 6.2 | 25 |
| S. mitis | L 1320$^{(3)}$ | 3.1 | 3.1 | 3.1 | 3.1 | 6.2 | 3.1 | 0.8 | 1.6 | 0.8 | 12.5 |
| S. faecalis D | L 1321$^{(3)}$ | 25 | 25 | 50 | 100 | 100 | 25 | 50 | 25 | 12.5 | 100 |
| S. viridans | L 1322$^{(3)}$ | 50 | 50 | 50 | 25 | 100 | 50 | 12.5 | 50 | 6.2 | 100 |
| S. salivarius | L 1323$^{(3)}$ | 0.4 | 0.4 | 0.8 | 0.8 | 6.2 | 0.4 | 0.05 | 0.8 | 0.05 | 3.1 |
| S. sanguis H | L 1324$^{(3)}$ | 50 | 25 | 50 | 50 | 100 | 50 | 12.5 | 50 | 6.2 | 100 |
| S. bovis D | L 1325$^{(3)}$ | 50 | 50 | 25 | 25 | 25 | 25 | 12.5 | 25 | 12.5 | 100 |

| MICROORGANISM | | X | XI | XII | XIII | XIV | XV | XVI | XVII |
|---|---|---|---|---|---|---|---|---|---|
| S. aureus TOUR | $10^{3(1)}$ | >100 | 50 | 50 | 50 | >100 | 100 | 100 | 100 |
|  | $10^{6(1)}$ | >100 | 100 | 100 | — | >100 | >100 | >100 | >100 |
|  | + serum$^{(2)}$ | >100 | 50 | 50 | — | 100 | 100 | 50 | 50 |
| S. pyogenes | C 203 | — | 1.6 | 3.1 | 0.8 | 6.2 | 6.2 | 3.1 | 3.1 |
| S. pneumoniae | UC 41 | >100 | 50 | 25 | 12.5 | 100 | 12.5 | 50 | 50 |
| S. mitis | L 1320$^{(3)}$ |  |  |  | 3.1 |  |  |  |  |
| S. faecalis D | L 1321$^{(3)}$ |  |  |  | 100 |  |  |  |  |
| S. viridans | L 1322$^{(3)}$ |  |  |  | 50 |  |  |  |  |
| S. salivarius | L 1323$^{(3)}$ |  |  |  | 0.8 |  |  |  |  |
| S. sanguis H | L 1324$^{(3)}$ |  |  |  | 50 |  |  |  |  |
| S. bovis D | L 1325$^{(3)}$ |  |  |  | 25 |  |  |  |  |

Notes to Table IV:
$^{(1)}$Inoculum (CFU/ml)
$^{(2)}$In the presence of 30% bovine serum
$^{(3)}$Clinical isolates.

The antimicrobial activity of the compounds of the invention is also confirmed in in vivo test in mices experimentally infected with S. pyogenes or S. pneumoniae. The experiments are conducted essentially as described by R. Pallanza et al., J. Antimicrob. Chemother. 11, 419 (1983).

The experimental infection was induced in mice by intraperitoneally administering a suspension of the test pathogens. Inocula had been adjusted so that the untreated animals died of septicemia within 48 h. Animals were treated subcutaneously with the test compound once a day for three days starting about 30 min after infection.

The $ED_{50}$ value was calculated on the $10^{th}$ day by the method of Spearman and Kärber (D. J. Finney "Statistical Method in Biological Assay", Griffin, page 524, 1952) on the basis of the percentage of survival at each dose. In the above conditions the $ED_{50}$ value of some representative compounds of the invention are reported below:

cells of S. pyogenes C 203. Compound III shows a good bactericidal activity comparable to that of actagardine, but at lower concentrations. For both antibiotics, 99% of killing effect was obtained after 5 h of incubation at doses 10 times the MIC, while 99.9% was reached in 24 h. For compound III, this level of killing action was obtained also at a dose equal to the MIC (0.4 ug/ml). This comparison was carried out on Todd-Hewitt broth(s) containing compound III and actagardine at concentrations equal to or multiple of the MIC which were inoculated with growing cells of S. pyogenes C 203 ($\sim 10^6$ CFU/ml). The cultures were incubated at 37° C. with shaking and viable cells were counted at intervals.

In view of the above the compounds of the present invention can effectively be employed as the active ingredient of antimicrobial preparations used in human and veterinary medicine for the prevention and treatment of infectious diseases caused by pathogenic bacteria which are susceptible to said active ingredients. In such treatments, these compounds may be employed as such or in the form of mixtures in any proportion. The compounds of the present invention can be administered topically or parenterally but, the parenteral administration is preferred. Depending on the route of administration, these compounds can be formulated into various dosage forms. For topical use the compounds of the present invention may also be prepared in suitable forms for absorption through the mucous membranes of the nose and throat or bronchial tissues and may conveniently take the form of liquid sprays or inhalants, lozanges, or throat paints. For medication of the eyes or ears, the preparation may be presented in liquid or semi-liquid form. Topical applications may be formulated in hydrophobic or hydrophilic bases as ointments, creams, lotions, paints, or powders.

Compositions for injection may take such forms as suspensions, solutions, or emulsions in oily or aqueous vehicles, and may contain formulatory agents such as suspending, stabilizing and/or dispersing agents.

Alternatively, the active ingredient may be in powder form for reconstitution at the time of delivery with a suitable vehicle, such as sterile water.

The amount of active principle to be administered depends on various factors such as the size and condition of the subject to be treated, the route and frequency of administration, and the causative agent involved.

The compounds of the invention are generally effective at a daily dosage comprised between about 0.5 and about 30 mg of active ingredient per Kg of body weight, preferably divided in 2 to 4 administrations per day.

Particularly desirable compositions are those prepared in the form of dosage units containing from about 20 to about 300 mg per unit.

Representative examples of preparation of pharmaceutical compositions are as follows:

A parenteral solution is prepared with 100 mg of compound III dissolved in 2 ml of sterile water for injection A parenteral solution is prepared with 250 mg of compound III dissolved in 3 ml of sterile water for injection A topical ointment is prepared with
200 mg of compound III
3.6 g of polyethylene glycol 4000 U.S.P.
6.2 g of polyethylene glycol 400 U.S.P.

Besides their activity as medicaments, the compounds of the present invention can be used as animal growth promoters.

For this purpose, one or more of the compounds of the invention is administered orally in a suitable feed. The exact concentration employed is that which is required to provide for the active agent in a growth promotant effective amount when normal amounts of feed are consumed.

The addition of the active compounds of the invention to animal feed is preferably accomplished by preparing an appropriate feed premix containing the active compounds in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and Co., S. Francisco, USA, 1969 or "Livestock Feeds and Feeding", O and B Books, Corvallis, Oreg., USA, 1977) and are incorporated herein by reference.

The following examples illustrate the manner in which the invention can be practiced, but, as such, should not be construed as limiting its overall scope.

EXAMPLE 1

Preparation of compounds I–IIIa and V–IX (general procedure):

To a stirred solution of 1 mmol of actagardine and 4 mmol of the proper di-amine in 100 ml of DMF a solution of 2.5 mmol of DPPA in 20 ml of DMF is added dropwise in 30 min while cooling at 0°–5° C. The reaction mixture is kept 6 h at 5° C. and overnight at room temperature. On adding 500 ml of ether a solid separates which is collected, washed with 100 ml of ether, and re-dissolved in 500 ml of a mixture n-butanol:water:methanol 45:45:10 (v/v/v). The organic layer is separated, washed with 100 ml of water and concentrated to a small volume under vacuum at 50° C. A solid is then precipitated by adding ether; it is then collected and washed with ether.

1 g of this crude material is dissolved in 60 ml of a mixture acetonitrile and 0.01M phosphate buffer pH 8, 85:15 (v/v), and the resulting solution is applied to a silica-gel (0.2–0.06 mm) column (200 g), eluting with the following mixtures of acetonitrile and 0.01M phosphate buffer pH 8 (v/v):

(a) 85/15 (0.2 l); (b) 80/20 (0.4 l); (c) 75/25 (0.8 l); (d) 70/30 (0.8 l); (e) 65/35 (0.8 l)

Fractions of about 50 ml are collected and monitored by TLC using *S. pyogenes* C 203 to individuate the active fractions. Fractions containing the active compound are pooled, one volume of n-butanol is added thereto and the solvents are evaporated under vacuum at room temperature until a butanolic solution residuates.

The residual butanolic solution is washed with water (three times) and then concentrated to a small volume under vacuum. Upon standing overnight at room temperature, and cooling if necessary, a solid separates which is collected washed with ether and dried under vacuum overnight at about 50° C.

The physico-chemical data of the obtained compounds are reported in Tables I, II, and III.

EXAMPLE 2

Preparation of compound IV (actagardine N-(2-aminoethyl)-1,2-ethanediamine monocarboxamide):

(a) preparation of 1,7-dibenzylidenediethylenetriamine.

Four mmol of diethylenetriamine are reacted with benzaldehyde (12 mmol) in ethanol (100 ml) at room temperature.

When the reaction is completed generally the reaction mixture is cooled, concentrated to a small volume and the product which precipitates is recovered by filtration.

(b) preparation of compound IV:

To a stirred solution of 1 mmol of actagardine and 4 mmol of 1,7-dibenzylidenediethylenetriamine in 100 ml of DMF, a solution of 2.5 mmol of DPPA in 20 ml of DMF is added dropwise in 30 min while cooling at 0°–5° C. The reaction mixture is kept 6 h at 5° C. and overnight at room temperature. On adding 500 ml of ether a solid separates which is collected, washed with 100 ml of ether, and re-dissolved in 500 ml of a mixture n-butanol:water:methanol 45:45:10 (v/v/v). The organic layer is separated, washed with 100 ml of water and concentrated to a small volume under vacuum at 50° C. A solid is precipitated by adding ether and is then collected, and washed with ether. 1 g of this crude material is dissolved in 60 ml of a mixture acetonitrile and 0.01M phosphate buffer pH 8, 85:15 (v/v), and the resulting solution is applied to a silica-gel (0.2–0.06 mm) column (200 g), eluting with the following mixtures of acetonitrile and 0.01M phosphate buffer pH 8 (v/v):

(a) 85/15 (0.2 l); (b) 80/20 (0.4 l); (c) 75/25 (0.8 l); (d) 70/30 (0.8 l); (e) 65/35 (0.8 l).

Fractions of about 50 ml are collected and monitored by TLC using *S. pyogenes* C 203 to individuate the active fractions.

The fractions which contain the active compound are pooled, one volume of n-butanol is added thereto and the solvents are evaporated under vacuum at room temperature until a butanolic solution residuates.

The residual butanolic solution is washed with water (three times) and then concentrated to a small volume. Upon standing overnight at room temperature, and cooling if necessary, a solid separates which is collected washed with ether and dried under vacuum overnight at about 50° C.

1 g of this product (which is the dibenzylidene derivative of the compound of the title) is dissolved in 200 ml of a mixture of 0.1N HCl: DMF 9:1 (v/v) at room temperature with stirring. After standing overnight at room temperature, 250 ml of n-butanol is added, the pH of the aqueous layer is brought to 7.0 with 3% aqueous NaHCO$_3$ and the organic layer is separated and concentrated to a small volume. On adding ether, a solid separates which is collected, washed with ether, and purified on a silica-gel (0.2–0.06 mm) column eluting with acetonitrile/0.01M phosphate buffer pH 8 as described above for the dibenzylidene derivative. The physico-chemical data are reported in Tables I, II and III.

EXAMPLE 3

Alternative preparation of compound VIII:

To a stirred solution of 1 mmol of actagardine and 4 mmol of cyclopentylpiperazine dihydrochloride in 100 ml of DMF 10 mmol of triethylamine is added while cooling at about 0° C. Then a solution of 2.5 mmol of DPPA in 20 ml of DMF is added dropwise in 30 min while keeping the temperature at 0°–5° C. The reaction mixture is then kept 6 h at about 5° C. and overnight at room temperature. On adding 500 ml of ether a solid separates which is collected, washed with 100 ml of ether, and re-dissolved in 500 ml of a mixture n-butanol:water:methanol 45:45:10 (v/v/v). The organic layer is separated, washed with 100 ml of water and concentrated to a small volume under vacuum at 50° C. A solid is then precipitated by adding ether and it is collected and washed with ether. 1 g of this crude material is dissolved in 60 ml of a mixture acetonitrile and 0.01M phosphate buffer pH 8, 85:15 (v/v), and the resulting solution is applied to a silica-gel (0.2–0.06 mm) column (200 g), eluting with the following mixtures of acetonitrile and 0.01M phosphate buffer pH 8 (v/v):

(a) 85/15 (0.2 l); (b) 80/20 (0.4 l); (c) 75/25 (0.8 l); (d) 70/30 (0.8 l); (e) 65/35 (0.8 l).

Fractions of about 50 ml are collected and monitored by TLC using *S. pyogenes* C 203 to individuate the active fractions.

Fractions containing the active compound are pooled, one volume of n-butanol is added thereto and the solvents are evaporated under vacuum at room temperature until a butanolic solution residuates.

The residual butanolic solution is washed with water (three times) and then concentrated to a small volume.

Upon standing overnight at room temperature, and cooling if necessary, a solid separates which is filtered off washed with ether and dried under vacuum overnight at about 50° C.

The physico-chemical data of the obtained compound are reported in Tables I, II and III.

EXAMPLE 4

Preparation of compound IIIb (actagardine 3,3-dimethylamino-1-propylamide monocarboxamide, hydrochloride):

To a stirred solution of 1 mmol of IIIa in 200 ml of water, 10 ml of 0.1N HCl is added dropwise while cooling at 5° C. The resulting solution, brought to about pH 5, is extracted with 400 ml of n-butanol.

The organic layer is separated and concentrated to a small volume at 35° C. under vacuum. On adding ether, the solid product of the title separates which is collected, washed with ether, and dried under vacuum overnight at 50° C.

The physico-chemical data are reported in Tables I, II and III.

EXAMPLE 5

Preparation of compounds X–XII and XIV–XVII (general procedure):

To a stirred suspension of the corresponding basic amide (namely: Co.I for Co.X, Co.III for Co.XI–XII, Co.VII for Co.XIV–XV and Co. VIII for Co.XVI–XVII) (1 mmole) in 400 ml of the proper alcohol R$^5$OH, 37% hydrochloric acid (about 4 ml) is added while stirring at room temperature. The final alcoholic solution is about 0.1M alcoholic HCl. The reaction course is monitored by TLC (on silica gel plates; silica gel 60-F$_{254}$ Merck; mobile phase: n-butanol/acetic acid/water, 4:1:1 (v/v/v). The reaction is generally completed in 24–96 h.

The resulting solution is concentrated under vacuum at 40°–50° C. The oily residue is washed with acetone and triturated to obtain a solid which is collected by filtration and washed with a mixture acetone/ethyl ether, 1:1 (v/v) and then with ether. This solid is then dried under vacuum over KOH pellets at room temperature for 24–48 h.

The obtained compounds are the hydrochlorides of the compounds of the title (yield=0.85–0.95 mmol; 85–95%).

The corresponding analytical pure free bases are prepared by column chromatography from the above hydrochlorides according to the following procedure: 1.5 g of the hydrochloride obtained above is dissolved in 60 ml of a mixture acetonitrile/water 85:15 (v/v), the resulting solution is adjusted to pH 6.5 with phosphate buffer and applied to a silica-gel (0.06–0.2 mm) column (200 g), eluting with a linear gradient from 15% to 40% of water in acetonitrile, in 20 h at rate of 200 ml/h.

Fractions of about 25 ml are collected and monitored by TLC. Fractions containing the free base compound are pooled, about one volume of n-butanol is added thereto and the solvents are evaporated under vacuum at room temperature until a butabolic solution residuates. The residual butanolic solution is washed with water (three times) and then concentrated to a small volume under vacuum.

Upon standing overnight at room temperature, and cooling if necessary, a solid separates which is collected, washed with ether and dried in the air for 2-3 days. The physico-chemical data of the obtained compounds are reported in Tables I, II, and III.

EXAMPLE 6

Preparation of compound XIII (N-ethyl actagardine 3,3-dimethylamino-1-propylamide monocarboxamide).

To a stirred solution of 1 mmol of IIIa in 300 ml of metanol, 0.45 ml of acetaldehyde is added dropwise while cooling to 0° C. The reaction mixture is stirred at 0° C. for 2 h, afterwards 0.3 g of NaBH₄ is added portionwise in 1 h. Stirring is continued for additional 2 h at room temperature, then NHCl is added at about pH 4. The resulting solution is poured into 900 ml of water while cooling at 5° C. After extraction with 900 ml of n-butanol, the organic layer is separated, washed with 500 ml of water and concentrated to a small volume at 40° C. under vacuum. On adding ether, the solid product of the title separates which is collected, washed with ether, and dried under vacuum overnight at 40° C. Yield 1.47 g. The physico-chemical data are reported in Table I, II, and II.

We claim:

1. Basic monoamide derivatives of actagardine of formula

wherein the group

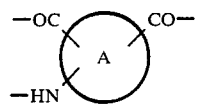

represents the actagardine nucleus, R represents the group

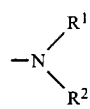

wherein $R^1$ and $R^2$ independently represents hydrogen, a group of formula

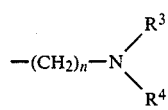

in which n represents an integer from 2 to 8 and $R^3$ and $R^4$ independently represent hydrogen or $(C_1-C_4)$alkyl or $R^3$ and $R^4$ taken together represent a —(CH₂)₃—, —(CH₂)₄—, —(CH₂)₂—O—(CH₂)₂—, —(CH₂)₂—S—(CH₂)₂—, or —(CH₂)₅— group, or $R^1$ and $R^2$ taken together with the adjacent nitrogen atom represent a piperazine moiety which may be substituted in position 4 with a substituent selected from $(C_1-C_4)$ alkyl, $(C_5-C_7)$ cycloalkyl, benzyl, and substituted benzyl wherein the phenyl moiety bears 1 or 2 substituents selected from chloro, bromo, nitro, $(C_1-C_4)$alkyl and $(C_1-C_4)$alkoxy, $R^5$ represents hydrogen, $(C_1-C_4)$alkyl, $(C_1-C_4)$alkoxy $(C_2-C_4)$alkyl, and $R^6$ represents hydrogen or $(C_1-C_4)$alkyl, with the proviso that $R^1$ and $R^2$ can not simultaneously represent hydrogen, and the acid and base addition salts thereof.

2. A compound according to claim 1 wherein R represents a group selected from:

—NH—(CH₂)₂NH₂;                —NH—(CH₂)₃NH₂
—NH—(CH₂)₄NH₂;                —NH—(CH₂)₃NHCH₃
—NH—(CH₂)₃N(CH₃)₂;           —NH—(CH₂)₃N(C₂H₅)₂
—NH(CH₂)₃N(C₃H₇)₂;           —NH—(CH₂)₃N(C₄H₉)₂
—NH—(CH₂)₅N(CH₃)₂;           —NH(CH₂)₆N(CH₃)₂
—NH(CH₂)₆NHCH₃;              —N[(CH₂)₂NH₂]₂
—N[(CH₂)₃NH₂]₂;               —N[(CH₂)₂N(CH₃)₂]₂
—N[(CH₂)₃N(CH₃)₂]₂;           —N[(CH₂)₄NH₂]₂

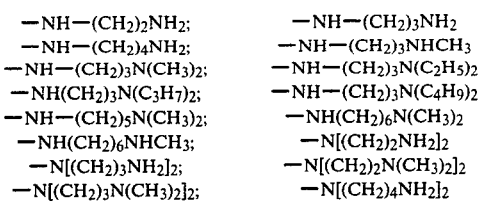

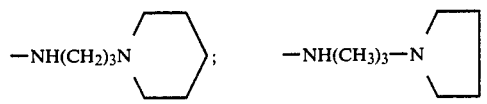

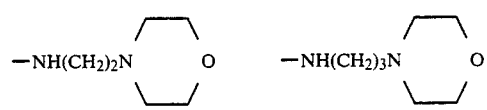

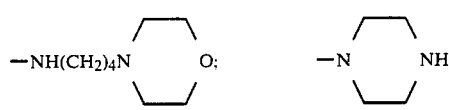

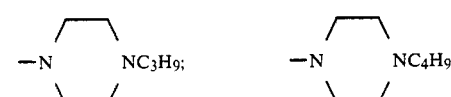

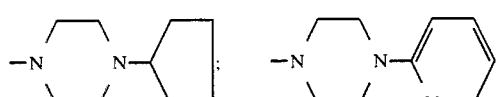

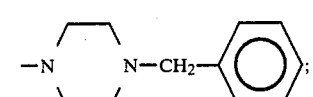

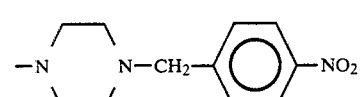

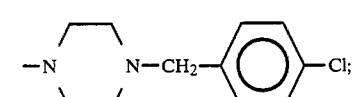

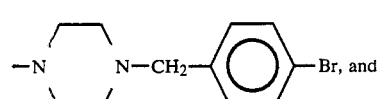

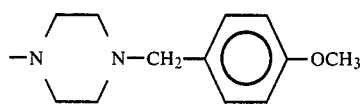

3. A compound according to claim 1 wherein R represents a group selected from:

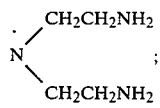
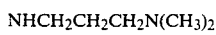
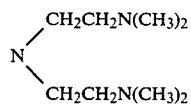
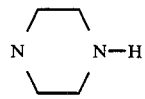
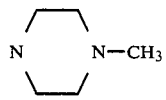

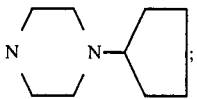
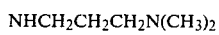

4. A compound according to claim 1 wherein R represents the group

NHCH$_2$CH$_2$CH$_2$N(CH$_3$)$_2$ or a corresponding pharmaceutically-acceptable acid addition salt.

5. A compound according to claims 1, 2, 3, or 4 wherein $R^5$ and $R^6$ represent hydrogen.

6. A compound according to claims 1, 2, 3, or 4 wherein $R^5$ represents hydrogen and $R^6$ represents (C$_1$-C$_4$)alkyl.

7. A pharmaceutical composition which comprises a compound of claims 1, 2, 3 or 4 in admixture with a pharmaceutically acceptable carrier.

* * * * *